United States Patent [19]
Lin et al.

[11] Patent Number: 5,705,731
[45] Date of Patent: Jan. 6, 1998

[54] REACTIVATION OF HYDROCARBON ISOMERIZATION CATALYSTS

[75] Inventors: Fan-Nan Lin, Bartlesville; Johnnie R. Pierce, Nowata; John D. Cowan, Bartlesville, all of Okla.

[73] Assignee: Phillips Petroleum Company, Bartlesville, Okla.

[21] Appl. No.: 568,109

[22] Filed: Dec. 6, 1995

[51] Int. Cl.$^6$ .................. B01J 20/34; C07C 5/13
[52] U.S. Cl. .................. 585/748; 502/53
[58] Field of Search .................. 585/748; 502/53

[56] References Cited

U.S. PATENT DOCUMENTS

| | | | |
|---|---|---|---|
| 2,583,740 | 1/1952 | Kemp | 260/683.5 |
| 3,248,320 | 4/1966 | White et al. | 208/136 |
| 3,527,715 | 9/1970 | Gianetti et al. | 252/415 |
| 3,551,516 | 12/1970 | Ashley et al. | 260/683.68 |
| 3,789,082 | 1/1974 | Cook et al. | 260/683.68 |
| 3,903,195 | 9/1975 | Franch et al. | 260/683.68 |
| 4,039,604 | 8/1977 | Myers et al. | 260/683.68 |
| 4,835,129 | 5/1989 | Travers et al. | 502/37 |
| 5,039,639 | 8/1991 | Khara | 502/36 |
| 5,212,128 | 5/1993 | Schorfheide et al. | 502/31 |
| 5,306,681 | 4/1994 | Schorfheide et al. | 502/22 |
| 5,463,166 | 10/1995 | Lin | 585/748 |
| 5,654,247 | 8/1997 | Lin et al. | 585/748 |

*Primary Examiner*—Ellen M. McAvoy
*Attorney, Agent, or Firm*—K. K. Brandes

[57] ABSTRACT

In a process for isomerizing $C_4$–$C_7$ alkanes and/or $C_6$–$C_7$ cycloalkanes which is carried out in the presence of hydrogen gas, a chloride additive (e.g., $CCl_4$ or $C_2Cl_4$) and a supported platinum and chlorine-containing catalyst (e.g., $Pt/Cl/Al_2O_3$), the catalyst is intermittently reactivated in two steps: first, the hydrogen to feed hydrocarbon ratio is raised (while the chloride level in the feed is either not changed or lowered), and thereafter the chloride level in the feed is increased. Preferably, the fresh catalyst is also preactivated by contacting it with the hydrocarbon feed wherein the hydrogen to feed hydrocarbon ratio is higher and/or the temperature is lower than what is employed in the subsequent isomerization production cycle.

30 Claims, No Drawings

REACTIVATION OF HYDROCARBON ISOMERIZATION CATALYSTS

BACKGROUND OF THE INVENTION

In one aspect, this invention relates to the intermittent reactivation of supported platina- and chlorine-containing catalysts for $C_4$–$C_7$ alkane and/or $C_6$–$C_7$ cycloalkane hydroisomerization (i.e., isomerization in the presence of hydrogen gas). In another aspect, this invention relates to $C_4$–$C_7$ alkane and/or $C_6$–$C_7$ cycloalkane hydroisomerization processes comprising preactivation and intermittent reactivation of the catalyst used therein.

Supported platinum catalysts are useful for the hydroisomerization of saturated hydrocarbons: $C_4$–$C_7$ alkanes (generally normal, i.e., linear, alkanes) and $C_6$–$C_7$ cycloalkanes. These catalysts are subject to deactivation as a result of prolonged usage for a variety of reasons. For example, dimers and oligomers of these alkanes can be formed as by-products. These by-products tend to accumulate on the catalyst surface and cause a decrease in catalytic isomerization activity. This invention is directed to the removal of these by-products and possibly other catalyst poisons (such as organic sulfur compounds) from used (i.e., partially deactivated) isomerization catalysts, thus substantially restoring the activity and prolonging the life of these catalysts. In addition, this invention is also concerned with the preactivation of a fresh (unused) isomerization catalyst, which thereafter undergoes reactivation (after it has been used and partially deactivated).

SUMMARY OF THE INVENTION

It is an object of this invention to provide a $C_4$–$C_7$ alkane and/or $C_6$–$C_7$ cycloalkane hydroisomerization process (i.e., isomerization in the presence of hydrogen gas) comprising an intermittent step of treating a partially deactivated, supported, Pt- and Cl-containing isomerization catalyst (in particular, a Pt/Cl/$Al_2O_3$ catalyst) so as to substantially enhance its catalytic activity. It is a further object of this invention to provide a $C_4$–$C_7$ alkane and/or $C_6$–$C_7$ cycloalkane hydroisomerization process comprising pretreatment of a Pt/Cl/$Al_2O_3$ catalyst (so as to enhance its initial catalytic activity) and intermittent treatment of the Pt/Cl/$Al_2O_3$ catalyst after it has been partially deactivated. Other objects and advantages will be apparent from the detailed description and the appended claims.

In accordance with this invention, a process for isomerizing saturated hydrocarbons comprises the steps of:

(A) contacting (a) a fluid feed mixture comprising (i) at least one saturated feed hydrocarbon selected from the group consisting of alkanes containing 4–7 carbon atoms per molecule and cycloalkanes containing 6–7 carbon atoms per molecule, (ii) hydrogen gas and (iii) at least one chlorinated hydrocarbon with an isomerization catalyst comprising platinum, chlorine (chemically bound as chloride) and an inorganic support material in a reaction zone at effective isomerization conditions comprising a reaction temperature in the range of about 80° F. to about 500° F., a molar ratio of hydrogen gas to said at least one saturated feed hydrocarbon in the range of about 0.02:1 to about 10:1, and a content of said at least one chlorinated hydrocarbon in said fluid feed mixture equivalent to a chloride (i.e., bound chlorine) level in the range of about 20 ppm Cl to about 800 ppm Cl, so as to convert a portion of said at least one saturated feed hydrocarbon to at least one saturated product hydrocarbon isomer for a prolonged period of time until said catalyst is partially deactivated;

(B) increasing the molar ratio of hydrogen gas to said at least one saturated feed hydrocarbon at least about 10 percent above said molar ratio employed in step (A) while substantially retaining the remaining operating conditions of step (A), and maintaining the operating conditions of this first reactivation step (B) for a time period of at least about 0.1 hour;

(C) increasing the content of said at least one chlorinated hydrocarbon in said fluid feed mixture at least about 10 percent above said content used in steps (A) and (B) while substantially retaining the remaining operating conditions of step (B), and maintaining the operating conditions of this second reactivation step (C) for a time period of at least about 0.1 hour; and (D) returning to said effective isomerization conditions (including said molar ratio and said content of at least one chlorinated hydrocarbon) employed in step (A), and carrying out the present isomerization step (D) using the reactivated catalyst obtained in step (C) until said reactivated catalyst is again partially deactivated.

When the reactivated catalyst is again partially deactivated in step (D), steps (B) and (C) are generally carried out again, this time using the partially deactivated catalyst from step (D). Preferably, steps (B), (C) and (D) are repeated at least once (i.e., once or twice or more often than twice).

Preferably, step (B) is carried out by additionally lowering (generally at least about 1 percent, preferably at least about 5 percent) the content of said at least one chlorinated hydrocarbon in said fluid feed mixture employed in step (A) (in addition to increasing the molar ratio of hydrogen gas to said at least one saturated feed, as described above) while substantially retaining the remaining operating conditions of step (A).

In a preferred embodiment, said process comprises the additional step of (X) preactivating said isomerization catalyst, before it is employed in step (A), by treating of said catalyst with said fluid feed mixture, wherein ($\alpha$) the molar ratio of hydrogen gas to said at least one saturated feed hydrocarbon in step (X) is at least about 20 percent (preferably about 50–500 percent) higher than said molar ratio employed in step (A) , or wherein ($\beta$) the reaction temperature in step (X) is at least about 5° F. lower than said reaction temperature employed in step (A), or wherein both operating parameters ($\alpha$) and ($\beta$) are applied in step (X).

Preferably, the pressure applied in step (X) and in steps (A) through (D) is about 50–2000 psig. In a preferred embodiment, the at least one saturated feed hydrocarbon is at least one normal alkane and the catalyst comprises (more preferably consists essentially of) platinum, chlorine and alumina (as the support). Free oxygen and oxygen-containing compounds (such as water, alcohols, ethers, aldehydes, ketones, carboxylic acids, etc.) to be substantially absent from all steps, i.e., from step (X) and from steps (A) through (D).

DETAILED DESCRIPTION OF THE INVENTION

Any effective isomerization catalyst (also referred to as "hydroisomerization catalyst" hereinafter) which contains Pt, Cl and a support (preferably alumina) can be used in the process of this invention. Such isomerization catalysts which catalyze the conversion of $C_4$–$C_7$ alkanes (such as n-butane) to isoalkanes (such as isobutane) and the isomerization of $C_6$–$C_7$ cycloalkanes (such as methylcyclopentane to cyclohexane or vice versa) are well known. These catalysts can be prepared by processes described in the patent literature, such as U.S. Pat. Nos. 3,449,264 and 4,014,948.

Catalysts for $C_4$, $C_5$ and $C_6/C_7$ alkane and also $C_6/C_7$ cycloalkane isomerization are commercially available from various catalyst manufacturers, e.g., from UOP, Inc., Des Plaines, Ill. Generally, these catalysts contain about 0.01–3 (preferably about 0.01–1) weight-% Pt on a suitable inorganic support, preferably alumina. The preferred n-butane isomerization catalysts further contain about 0.5–10 (preferably about 2–6) weight-% Cl. The term "partially deactivated alkane isomerization catalyst", as used herein, refers to an alkane isomerization catalyst which has been employed in n-alkane hydroisomerization steps (A) and (F), respectively, and has lost a portion (generally about 5–20%) of its initial isomerization activity. At this point the catalyst has been deactivated to the extent that the catalyst no longer satisfies the desired conversion/selectivity requirement for the saturated hydrocarbon isomerization process. The weight percentages of Pt and of Cl in the partially deactivated catalyst are essentially the same as those in the fresh catalyst.

Saturated feed hydrocarbons which can be employed in the process of this invention include (but are not limited to) n-butane, n-pentane, n-hexane, n-heptane, 2-methylpentane, 2-methylhexane, 3-methylhexane, methylcyclopentane, cyclohexane, methylcyclohexane and mixtures of any two or more than two of the above-listed saturated hydrocarbons. Presently preferred hydrocarbons are n-butane and n-heptane. These feed hydrocarbons are isomerized to isomers at effective isomerization conditions, for instance, n-butane (normal-butane) is isomerized to isobutane (2-methylpropane); n-pentane is isomerized to 2-methylbutane and 2,2-dimethylpropane; n-hexane is isomerized to 2-methylpentane, 3-methylpentane, 2,2-dimethylbutane, 2,3-dimethylbutane; n-heptane is isomerized to 2-methylhexane, 3-methylhexane, 2,2-dimethylpentane, 2,3-dimethylpentane, 2,4-dimethylpentane, 3,3-dimethylpentane, 3-ethylpentane; methylcyclopentane is isomerized to cyclohexane and vice versa (depending on which cycloalkane is present at the higher concentration in the feed); and methylcyclohexane is isomerized to 1,2-dimethylcyclopentane, 1,3-dimethylcyclopentane, 1,4-dimethylcyclohexane, trimethylcyclopentane, and the like.

The basic isomerization conditions in step (A), and also in step (D), are well known and can be varied to achieve the desired conversion in a manner known in the art. The recovery of the product isomer(s) from step (A), and also from step (D), as defined above, can be easily determined by those skilled in the art of alkane and cycloalkane isomerization and gas-gas and gas-liquid separations. In step (A), and also step (D), the saturated feed and $H_2$ are contacted with a catalyst (generally present in a fixed bed), at a reaction temperature of about 80°–500° F., preferably at a temperature of about 100°–450° F. In the more preferred case of n-alkane (in particular, n-butane) isomerization in the presence of $H_2$ gas, the average reaction temperature in the catalyst bed generally is about 250° F. to about 400° F. The hydrogen-to-alkane molar ratio used in the hydrocarbon hydroisomerization process generally is within the range of about 0.02:1 to about 10:1, preferably about 0.05:1 to about 6:1. Generally, the liquid hourly space velocity of the alkane feed stream, (i.e., cc of liquid feed per cc of catalyst per hour) is about 0.1 to about 15, and the reaction pressure in the isomerization zone generally is within the range of 50 psig to about 2000 psig (preferably about 100–800 psig). The gas hourly space velocity of the hydrogen stream is generally about 10–2,000 (preferably about 50–1000) cc $H_2$ per cc catalyst per hour (so as to give the above-recited $H_2$:alkane ratio).

In order to retard the catalyst deactivation in the isomerization step (A), and also in step (D), at least about 0.001 weight-% (i.e., about 10 ppm) chloride, generally about 15–800 ppm chloride (preferably about 20–400 ppm Cl) is added to the fluid feed, generally in the form of at least one chlorinated hydrocarbon (selected from the group consisting of chloroalkanes, chloroalkenes and chlorocycloalkanes) containing up to 6 carbon atoms and up to 8 chlorine atoms per molecule, such as monochloromethane, dichloromethane, trichloromethane (chloroform), tetrachloromethane (carbon tetrachloride; presently preferred), monochloroethane, dichloroethanes, trichloroethanes, tetrachloroethanes, pentachloroethane, hexachloroethane, monochloropropanes, dichloropropanes, trichloropropanes, tetrachloropropanes, pentachloropropanes, hexachloropropanes, heptachloropropanes, octachloropropane, monochlorobutane, dichlorobutanes, trichlorobutanes, tetrachlorobutanes, monochloropentane, dichloropentanes, trichloropentanes, tetrachloropentanes, monochlorohexane, dichlorohexanes, trichlorohexanes, tetrachlorohexanes, monochlorocyclopentane, dichlorocyclopentanes, trichlorocyclopentanes, monochlorocyclohexane, dichlorocyclohexanes, trichlorocyclohexanes, monochloroethylene, 1,1-dichloroethylene, 1,2-dichloroethylene, trichloroethylene, tetrachloroethylene (perchloroethylene, PCE; presently also preferred), chloropropylenes, chloro-n-butenes, chloroisobutenes, chloropentenes, mixtures comprising any of the above organic chloride compounds, and mixtures comprising HCl and any of the above organic chloride compounds.

Generally, isomerization production step (A) or, alternatively, step (D) can be carried out at satisfactory product isomer yields for a time period of about 3 days to about 6 months, in particular about 14–90 days, depending on the particular operating conditions, before the catalyst is deactivated to an extent that a satisfactory product yield can no longer be attained. Then the reactivation steps (B) and (C) are carried out. Satisfactory product isomer yields in step (A), or step (D), generally range from about 20% to about 90%, preferably about 40% to about 70%, depending on the particular feed hydrocarbon and the particular operating conditions.

In the first reactivation (rejuvenation) step (B) of this invention, the partially deactivated, supported, Pt-containing alkane isomerization catalyst used in isomerization production step (A) or, alternatively, in isomerization production step (D), is contacted with a fluid feed mixture which is substantially the same as that employed in step (A) or, step (D), except that the molar ratio of hydrogen gas to saturated feed hydrocarbon(s) has been increased at least about 10%, preferably about 20–200%, more preferably about 50–120%. For example, if the molar $H_2$:hydrocarbon ratio is about 1:1 in step (A) or, alternatively, in step (D), this ratio should be at least about 1.1:1, preferably about 1.2:1 to about 3:1, more preferably about 1.5:1 to about 2.2:1 in step (B). The chloride levels in step (A) or (D) and in step (B) can be substantially the same. Preferably, however, the added chloride level in step (B) has been lowered at least about 5%, compared with the chloride level of step (A) or, alternatively, step (D), more preferably about 40–90%. For example, if the added Cl level in the feed of step (A) or alternatively, step (D) is about 200 ppm Cl, the Cl level in this preferred feature of step (B) should preferably be about 190 ppm Cl, more preferably about 20–120 ppm Cl. Generally, step (B) is carried out for a time period of at least 0.1 hour, preferably about 0.5 hour to about 15 days, more preferably about 1 hour to about 7 days, depending on the specific operating conditions of step (B).

After reactivation step (B) has been completed, reactivation step (C) is started. The operating conditions of step (C) are substantially the same as those in step (B), except that the chloride (Cl) level has been adjusted so as to be at least about 10% higher than the chloride level in step (A) or, alternatively, step (D). Preferably, the Cl level in step (C) is about 20–300% higher than the Cl level employed in step (A) or (D), and more preferably about 50–100% higher than the Cl level employed in step (A) or (D). For instance, if the chloride level in step (A) or (D) is about 200 ppm Cl, the Cl level in step (C) should be at least about 220 ppm Cl, preferably about 240–600 ppm Cl, more preferably about 300–400 ppm Cl. The molar ratio of $H_2$ to feed hydrocarbon (s) in step (C) is essentially the same as the one employed in step (B). Generally step (C) is carried out for a time period of at least about 0.1 hour, preferably about 0.5 hour to about 15 days, more preferably about 1 hour to about 7 days, depending on the specific operating conditions of step (C). Thereafter, step (D), i.e., the regular isomerization production cycle employing the reactivated catalyst obtained in step (C), is carried out.

In a preferred embodiment of this invention, a fresh isomerization catalyst is pretreated, before it is employed in isomerization step (A), at conditions which are substantially the same as those employed in step (A) except that: (α) the molar ratio of hydrogen gas to feed hydrocarbon(s) is at least about 20% higher, preferably about 50–500% higher, more preferably about 100–200% higher, than the corresponding molar ratio which is to be employed in step (A), and/or (β) the operating temperature in this pretreatment step (X) is at least about 5° F. lower, preferably about 20°–40° F. lower, than the corresponding operating temperature which is to be employed in step (A). Generally, this preactivation step, before step (A), is carried out for at least about 4 hours, preferably about 6 hours to about 10 days, more preferably about 12 hours to about 5 days.

The following examples are presented to further illustrate the invention and are not to be considered as unduly limiting the scope of the invention.

EXAMPLE I

In this example, lab-scale tests are described to illustrate the preactivation step of the process of this invention.

In this Control Run 1 (without preactivation of the catalyst), a stainless-steel reactor (having an inner diameter of about 0.75 inch and a height of about 31 inches) was filled with a layer (14 inches high) of Alundum (inert alumina particles having a surface area of 1 $m^2/g$ or less), a layer (10 inches high) of unused (fresh) isomerization catalyst (marketed by UOP Inc., De Plains, Ill., under the product designation "I-8"; containing about 0.25 weight-% Pt and about 4 weight-% Cl on gamma-alumina; surface area: 165 $m^2/g$) and a bottom layer (12 inches high) of Alundum. The reactor contents were heated to about 310° F., and liquid normal butane was introduced into the reactor at a liquid hourly space velocity (LHSV) of about 4.0 cc/cc catalyst/hour, together with hydrogen gas at a flow rate of about 124 cc/minute, so as to provide a 0.4:1 molar ratio of $H_2$ to n-butane. The reaction pressure was about 450 psig. Carbon tetrachloride was added to the n-butane feed so as to attain a chloride level of about 250 ppm Cl. The obtained isomerization product (containing isobutane and unconverted n-butane) was analyzed at various time intervals by means of a gas chromatograph.

Invention Run 2 was carried out essentially as described for control Run 1, except that prior to the production cycle (at 310° F.; LHSV of 4; $H_2$:n-butane molar ratio of 0.4:1; 250 ppm added Cl), the fresh I-8 catalyst had been treated for 5 hours at a temperature of about 270°–290° F. with a $H_2$/n-butane feed mixture having a $H_2$:n-butane molar ratio of about 1:1 and containing 250 ppm Cl (added in the form of $CCl_4$).

Control Run 3 was essentially the same as control Run 1 except that the LHSV of n-butane was 12.0 (in lieu of 4.0) cc/cc catalyst/hour.

Invention Run 4 was essentially the same as control Run 3 except that prior to the above-described production cycle (at 310° F.; LHSV of 12; $H_2$:n-butane molar ratio of 1:1; 250 ppm added Cl), the "I-8" catalyst had been treated for 5 hours at a temperature of about 270°–290° F. with a feed mixture having a $H_2$ to n-butane molar ratio of 12:1 and containing 250 ppm Cl.

Pertinent test results are summarized in Table I.

TABLE I

| Run | Catalyst Preactivation | Time on Stream (Hours) | Isobutane PR[1] (%) |
|---|---|---|---|
| 1 (Control) | No | 0 | 50.9 |
| | | 20 | 51.2 |
| | | 40 | 47.9 |
| | | 80 | 45.4 |
| | | 96 | 45.3 |
| 2 (Invention) | Yes | 0 | 46.7 |
| | | 18 | 45.8 |
| | | 42 | 51.4 |
| | | 78 | 49.3 |
| | | 96 | 50.7 |
| 3 (Control) | No | 0 | 34.0 |
| | | 8 | 15.8 |
| | | 16 | 3.4 |
| 4 (Invention) | Yes | 0 | 33.4 |
| | | 8 | 38.3 |
| | | 16 | 40.1 |

[1]Product Ratio; defined as weight of isobutane in isomerization product divided by (weight of isobutane in product + weight of unconverted n-butane in product) times 100

Test data in Table I clearly show the benefit (namely less rapid catalyst deactivation) of the above-described preactivation of a fresh $Pt/Cl/Al_2O_3$ catalyst (I-8) at about 270°–290° F. with a $H_2$/n-butane feed mixture having a molar ratio of 1:1 before the isomerization production cycle (at 310° F., $H_2$/n-butane ratio of 0.4:1) was carried out.

The beneficial effect of the above-described preactivation of a fresh I-8 has been confirmed in a commercial n-butane isomerization process (at a refinery of Phillips Petroleum Company). The preactivation phase in this plant run was carried out for 3 weeks at a temperature of 240°–260° F., a $H_2$/n-butane molar ratio of 0.6:1, and addition of 200 ppm Cl (as $CCl_4$), whereas the production phase was carried out at a temperature of about 300°–310° F., a $H_2$:n-butane molar ratio of about 0.2:1, a n-butane LHSV of about 5.7 cc/cc catalyst/hour, and addition of about 100 ppm Cl (as $CCl_4$). The isobutane PR (defined in Table I) was about 45% during the preactivation cycle and about 51% during the production cycle. Thus, essentially no catalyst deactivation occurred during an initial plant production cycle which lasted about 5 weeks. In previous isomerization plant runs without a catalyst preactivation phase, catalyst deactivation problems were observed after about three weeks on stream (which had to be compensated for by increasing the production temperature from about 300° F. initially to about 320° F. toward the end of the cycle).

Additional preliminary lab tests, in which methylcyclopentane was isomerized to cyclohexane (at substantially the same preactivation and isomerization conditions as those described for Run 2), also indicated that a substantially reduced isomerization aleactivation of an "I-8" isomerization catalyst in the subsequent isomerization production cycle was realized.

EXAMPLE II

This example illustrates a n-butane isomerization process including the intermittent two-phase reactivation of a partially deactivated Pt/Cl/Al$_2$O$_3$ isomerization catalyst in accordance with the present invention.

In each of the following lab tests (using the reactor described in Example I), a fresh Pt/Cl/Al$_2$O$_3$ catalyst (UOP's "I-8", described above) was first preactivated for 18 hours at a temperature of 280° F., and a pressure of 450 psig with a H$_2$/n-butane isomerization feed mixture having a molar H$_2$/n-butane ratio of 1:1 and containing 400 ppm Cl (added as CCl$_4$). During this preactivation cycle, the isobutane product ratio (PR, defined in Table I) was about 23.5%. An isomerization production phase followed for about 90 hours at the following isomerization conditions: temperature of 280° F., pressure of 450 psig, molar H$_2$/n-butane ratio of 0.13:1; LHSV of n-butane of 4.0 cc/cc/hour; addition of 200 ppm Cl (as CCl$_4$). During this production cycle, the isobutane PR value decreased from about 55% (after about 6 hours on stream) to about 53% (after about 93 hours on stream). Then a reactivation cycle comprising two phases were carried out at conditions summarized in Table II. Thereafter, the isomerization cycle was resumed. Pertinent operating parameters and test remits are summarized in Table II.

than in corresponding control runs (which did not employ a Cl level in the first reactivation phase which was lower than the Cl level in the second reactivation phase).

The beneficial effect of the reactivation method of this invention has been confirmed in a commercial n-butane isomerization process (at a refinery of Phillips Petroleum Company). This n-butane isomerization plant operation included preactivation of a fresh "I-8" catalyst (as described in the penultimate paragraph of Example I), isomerization production cycles (substantially at conditions described in the penultimate paragraph of Example I, except that the H$_2$/n-butane molar ratio was 0.25:1 and the chloride level was about 100 ppm Cl) each of which lasted about 3 weeks, and two-phase reactivation cycles (wherein each phase lasted about 3 days, the H$_2$/n-butane molar ratio in both phases was about 0.6:1, CCl$_4$ addition during the first reactivation phase was equivalent to about 50 ppm Cl, and CCl$_4$ addition during the second reactivation phase was equivalent to about 150 ppm Cl). During this plant run, which lasted about 4 months, only minor catalyst deactivation was observed (as evidenced by the necessity of only a modest increase of the operating temperature from about 288° F. to about 290° F., so as to attain the desired isobutane PR value of 55%). In previous plant runs, which did not include the above-described preactivation and reactivation cycles (in accordance with this invention), generally the operating temperature had to be increased from about 302° F. to about 324° F. during the same time period so as to compensate for catalyst deactivation and to retain an isobutane PR value of about 56%.

EXAMPLE III

This example illustrates a n-heptane isomerization process, including preactivation and intermittent reactivation of a Pt/Cl/Al$_2$O$_3$ isomerization catalyst.

TABLE II

| | First Reactivation Phase[1] | | | Second Reactivation Phase[2] | | | Production Cycle[3] | | | |
|---|---|---|---|---|---|---|---|---|---|---|
| Run | n-Butane LHSV | H$_2$:n-Butane Molar Ratio | ppm Cl Added | n-Butane LHSV | H$_2$:n-Butane Molar Ratio | ppm Cl Added | n-Butane LHSV | H$_2$:n-Butane Molar Ratio | ppm Cl Added | Isobutane PR % |
| 5 (Control) | 4.0 | 0.4:1 | 200 | 4.0 | 0.4:1 | 200 | 4.0 | 0.2:1 | 200 | 50.7 |
| 6 (Control) | 4.0 | 0.4:1 | 266 | 4.0 | 0.4:1 | 133 | 4.0 | 0.2:1 | 200 | 48.8 |
| 7 (Invention) | 4.0 | 0.4:1 | 133 | 4.0 | 0.4:1 | 266 | 4.0 | 0.2:1 | 200 | 53.3 |

[1]duration: 30 minutes; temperature: 280° F.; pressure: 450 psig
[2]duration: 30 minutes; temperature: 280° F.; pressure: 450 psig
[3]duration: 2 hours; temperature: 280° F.; pressure: 450 psig; isobutane PR (defined in Table I) measured after 2 hours on stream Test data in Table II demonstrate the superiority of the reactivation method comprising lower chloride addition during the first reactivation phase and higher chloride addition during the second reactivation phase in accordance with this invention (Run 7) over reactivation methods outside the scope of this invention comprising either equal chloride addition in both reactivation phases (Run 5) or higher chloride addition during the first phase and lower chloride addition during the second phase (Run 6).

An additional invention run employed isomerization and reactivation conditions which were substantially the same as those described for invention Run 7, except that the Cl level in the first reactivation phase (i.e., step (B), as defined above) was about the same as the Cl level employed in the production cycle (i.e., step (A) or (D), as defined above). The Cl level in the second reactivation phase, i.e., in step (C), was higher than the Cl level employed in steps (A), (B) and (D), as defined above. Results of this additional invention run indicated that a higher isobutane PR value was attained In each of the following lab tests (using the reactor described in Example I), a fresh Pt/Cl/Al$_2$O$_3$ catalyst (UOP's "I-8"; described above) was first preactivated for 18 hours at 200° F./400 psig with a heptane feed (LHSV: 4.0 cc/cc/hour; containing about 25 weight-% n-heptane, about 23 weight-% 2-methylhexane, about 32 weight-% 3-methylhexane, about 5 weight-% 3-ethylpentane, about 8 weight-% 2,3-dimethylpentane, and about 6 weight-% cyclic hydrocarbons such as toluene) and hydrogen gas at a molar ratio of H$_2$ to the above-described heptane feed of 2:1. About 188 ppm Cl (as tetrachloroethylene) had been added to the feed. During this preactivation phase, the conversion of n-heptane (contained in the feed) to various isoheptanes was about 12%, and the 2,4-DMP/n-heptane ratio (described below) was about 0.31–0.37:1

An isomerization cycle followed for about 6 hours at the following isomerization conditions: temperature of 210° F., pressure of 400 psig, molar H$_2$/heptane-containing feed ratio of 0.53:1, LHSV of heptane feed of 1.25 cc/cc/hour, addition of 154 ppm Cl (added as tetrachloroethylene). During this isomerization run, about 52% of n-heptane was converted to isoheptanes. Since the feed contained only a minute amount (about 0.1%) of 2,4-dimethylpentane 2,4-DMP, the weight ratio of 2,4-dimethylpentane contained in the product to unconverted n-heptane contained in the product was used as the most sensitive indicator of the activity of the isomerization catalyst. At the end of the 6 hour isomerization cycle, the 2,4-DMP/n-heptane ratio was about 0.82:1.

Thereafter, reactivation cycles comprising two phases were carried out at conditions summarized in Table III. Then the isomerization cycle (at the above-described conditions) was resumed. Pertinent operating parameters and test results are summarized in Table III.

TABLE III

| | First Reactivation Phase[1] | | | Second Reactivation Phase[2] | | | Production Cycle[3] | | | |
|---|---|---|---|---|---|---|---|---|---|---|
| Run | LHSV of Hydrocarbon Feed | Molar Ratio of $H_2$ to Hydrocarbons | ppm Cl Added | LHSV of Hydrocarbon Feed | Molar Ratio of $H_2$ to Hydrocarbons | ppm Cl Added | LHSV of Hydrocarbon Feed | Molar Ratio of $H_2$ to Hydrocarbons | ppm Cl Added | 2,4 DMP to n-Heptane Ratio |
| 8 | — | — | — | — | — | — | 1.25 | 0.53:1 | 154 | 0.82 |
| 9 | 1.25 | 1.1:1 | 257 | 1.25 | 1.1:1 | 103 | 1.25 | 0.53:1 | 154 | 0.79 |
| 10 | 1.25 | 1.1:1 | 103 | 1.25 | 1.1:1 | 257 | 1.25 | 0.53:1 | 154 | 0.93 |

[1]duration: 1 hour; temperature: 210° F.; pressure: 400 psig
[2]duration: 1 hour; temperature: 210° F.; pressure: 400 psig
[3]duration: 6 hours; temperature: 210° F.; pressure: 400 psig; ratio of 2,4-DMP to unconverted n-heptane in the isomerization product was measured after 6 hours on stream Test data in Table III clearly demonstrate the beneficial effect of the reactivation method according to this invention of employing lower chloride addition during the first reactivation phase and higher chloride addition during the second reactivation phase in accordance with this invention (Run 10) versus no reactivation (Control Run 8) and versus a reactivation method employing higher chloride addition during the first reactivation phase and lower chloride addition during the second reactivation phase (Control Run 9).

An additional n-heptane isomerization lab test series (not described in detail herein) comprising catalyst preactivation and intermittent reactivation cycles in accordance with this invention (substantially at the above-described operating conditions, except that the molar $H_2$:hydrocarbon ratio during both reactivation cycles was about 4:1), also showed essentially no catalyst reactivation: the 2,4-DMP/n-heptane ratio in the isomerization product was 1.03:1 at the beginning of the test series and 1.01:1 at the end of the test series after about 530 hours on stream.

Reasonable variations, modifications and adaptations for various usages and conditions can be made within the scope of the disclosure and the appended claims, without departing from the scope of this invention.

That which is claimed is:

1. A process for isomerizing saturated hydrocarbons which comprises the steps of:
   (A) contacting (a) a fluid feed mixture comprising (i) at least one saturated feed hydrocarbon selected from the group consisting of alkanes containing 4–7 carbon atoms per molecule and cycloalkanes containing 6–7 carbon atoms per molecule, (ii) hydrogen gas and (iii) at least one chlorinated hydrocarbon with (b) an isomerization catalyst comprising platinum, chlorine and an inorganic support material in a reaction zone at effective isomerization conditions comprising a reaction temperature in the range of about 80° F. to about 500° F., a molar ratio of hydrogen gas to said at least one saturated feed hydrocarbon in the range of about 0.02:1 to about 10:1, and a content of said at least one chlorinated hydrocarbon in said fluid feed mixture equivalent to a chloride level in the range of about 15 ppm Cl to about 800 ppm Cl, so as to convert a portion of said at least one saturated feed hydrocarbon to at least one saturated product hydrocarbon isomer for a prolonged period of time until said catalyst is partially deactivated;
   (B) increasing the molar ratio of hydrogen gas to said at least one saturated feed hydrocarbon at least about 10 percent above said molar ratio employed in step (A) while substantially retaining the remaining operating conditions of step (A), and maintaining the operating conditions of this first reactivation step (B) for a time period of at least about 0.1 hour;
   (C) increasing the content of said at least one chlorinated hydrocarbon in said fluid feed mixture at least about 10 percent above said content used in steps (A) and (B) while substantially retaining the remaining operating conditions of step (B), and maintaining the operating conditions of this second reactivation step (C) for a time period of at least about 0.1 hour; and
   (D) returning to said effective isomerization conditions employed in step (A), and carrying out this isomerization step (D) using the reactivated catalyst from step (C) until said reactivated catalyst is again partially deactivated.

2. A process in accordance with claim 1, wherein the pressure in steps (A), (B), (C) and (D) is in the range of about 50 psig to about 2,000 psig.

3. A process in accordance with claim 1, wherein steps (B), (C) and (D) are repeated at least once.

4. A process in accordance with claim 1, wherein said at least one saturated feed hydrocarbon is selected from the group consisting of n-butane, n-pentane, n-hexane, n-heptane, 2-methylpentane, 2-methylhexane, 3-methylhexane, methylcyclopentane, cyclohexane, methylcyclohexane and mixtures thereof.

5. A process in accordance with claim 4, wherein said at least one chlorinated hydrocarbon is selected from the group consisting of chloroalkanes, chloroalkenes and chlorocycloalkanes and contains up to 6 carbon atoms and up to 8 chlorine atoms per molecule.

6. A process in accordance with claim 5, wherein said at least one saturated feed hydrocarbon is n-butane or n-heptane, and said at least one chlorinated hydrocarbon is carbon tetrachloride or perchloroethylene.

7. A process in accordance with claim 5, wherein said effective isomerization conditions in steps (A) and (D)

comprise a reaction temperature of about 100°–450° F., a molar ratio of hydrogen gas to said at least one saturated feed hydrocarbon of about 0.05:1 to about 6:1, a content of said at least one chlorinated hydrocarbon equivalent to a chloride level of about 15–800 ppm Cl, and a reaction pressure of about 100–800 psig.

8. A process in accordance with claim 5, wherein the molar ratio of hydrogen to said at least one saturated feed hydrocarbon in steps (B) and (C) is about 20–200% higher than said molar ratio employed in step (A) or, alternatively, step (D).

9. A process in accordance with claim 8; wherein the chloride level in step (C) is about 20–300% higher than said chloride level employed in step (A) or, alternatively, step (D).

10. A process in accordance with claim 9, wherein the time period of step (B) is about 0.5 hour to about 15 days and the time period of step (C) is about 0.5 hour to about 15 days.

11. A process in accordance with claim 1, comprising the additional step (X) of preactivating said isomerization catalyst, before it is employed in step (A), by treating of said catalyst with said fluid feed mixture, wherein (α) the molar ratio of hydrogen gas to said at least one saturated feed hydrocarbon in step (X) is at least about 20 percent higher than said molar ratio employed in step (A), or wherein (β) the reaction temperature in step (X) is at least about 5° F. lower than said reaction temperature employed in step (A), or wherein both operating parameters (α) and (β) are applied in step (X).

12. A process in accordance with claim 11, wherein the pressure in steps (X), (A), (B), (C) and (D) is in the range of about 50 psig to about 2,000 psig.

13. A process in accordance with claim 12, wherein said at least one saturated feed hydrocarbon is selected from the group consisting of n-butane, n-pentane, n-hexane, n-heptane, 2-methylpentane, 2-methylhexane, 3-methylhexane, methylcyclopentane, cyclohexane, methylcyclohexane and mixtures thereof.

14. A process in accordance with claim 13, wherein said at least one chlorinated hydrocarbon is selected from the group consisting of chloroalkanes, chloroalkenes and chlorocycloalkanes and contains up to 6 carbon atoms and up to 8 chlorine atoms per molecule.

15. A process in accordance with claim 14, wherein (α) said molar ratio of hydrogen gas to said at least one saturated feed hydrocarbon in step (X) is about 50–500% higher than said molar ratio employed in step (A) , or wherein (β) said reaction temperature employed in step (X) is about 20°–40° F. lower than said reaction temperature in step (A), or wherein both operating parameters (α) and (β) are applied in step (X), and wherein step (X) is carried out for at least 4 hours.

16. A process for isomerizing saturated hydrocarbons which comprises the steps of:
contacting (a) a fluid feed mixture comprising (i) at least one saturated feed hydrocarbons elected from the group consisting of alkanes containing 4–7 carbon atoms per molecule and cycloalkanes containing 6–7 carbon atoms per molecule, (ii) hydrogen gas and (iii) at least one chlorinated hydrocarbon with (b) an isomerization catalyst comprising platinum, chlorine and an inorganic support material in a reaction zone at effective isomerization conditions comprising a reaction temperature in the range of about 80° F. to about 500° F., a molar ratio of hydrogen gas to said at least one saturated feed hydrocarbon in the range of about 0.02:1 to about 10:1, and a content of said at least one chlorinated hydrocarbon in said fluid feed mixture equivalent to a chloride level in the range of about 15 ppm Cl to about 800 ppm Cl, so as to convert a portion of said at least one saturated feed hydrocarbon to at least one saturated product hydrocarbon isomer for a prolonged period of time until said catalyst is partially deactivated;

(B) increasing the molar ratio of hydrogen gas to said at least one saturated feed hydrocarbon at least about 10 percent above said molar ratio employed in step (A) and lowering by at least about 5 percent the content of said at least one chlorinated hydrocarbon in said fluid feed mixture employed in step (A) while substantially retaining the remaining operating conditions of step (A), and maintaining the operating conditions of this first reactivation step (B) for a period of at least about 0.1 hour;

(C) increasing the content of said at least one chlorinated hydrocarbon in said fluid feed mixture at least about 10 percent above said content used in steps (A) and (B) while substantially retaining the remaining operating conditions of step (B), and maintaining the operating conditions of this second reactivation step (C) for a time period of at least about 0.1 hour; and (D) returning to said effective isomerization conditions employed in step (A) and carrying out this isomerization step (D) using the reactivated catalyst from step (C) until said reactivated catalyst is again partially deactivated.

17. A process in accordance with claim 16, wherein the pressure in steps (A), (B), (C) and (D) is in the range of about 50 psig to about 2,000 psig.

18. A process in accordance with claim 16, wherein steps (B), (C) and (D) are repeated at least once.

19. A process in accordance with claim 16, wherein said at least one saturated feed hydrocarbon is selected from the group consisting of n-butane, n-pentane, n-hexane, n-heptane, 2-methylpentane, 2-methylhexane, 3-methylhexane, methylcyclopentane, cyclohexane, methylcyclohexane and mixtures thereof.

20. A process in accordance with claim 19, wherein said at least one chlorinated hydrocarbon is selected from the group consisting of chloroalkanes, chloroalkenes and chlorocycloalkanes and contains up to 6 carbon atoms and up to 8 chlorine atoms per molecule.

21. A process in accordance with claim 20, wherein said at least one saturated feed hydrocarbon is n-butane or n-heptane, and said at least one chlorinated hydrocarbon is carbon tetrachloride or perchloroethylene.

22. A process in accordance with claim 20, wherein said effective isomerization conditions in steps (A) and (D) comprise a reaction temperature of about 100°–450° F., a molar ratio of hydrogen gas to said at least one saturated feed hydrocarbon of about 0.05:1 to about 6:1, a content of said at least one chlorinated hydrocarbon equivalent to a chloride level of about 15–800 ppm Cl, and a reaction pressure of about 100–800 psig.

23. A process in accordance with claim 20, wherein the molar ratio of hydrogen to said at least one saturated feed hydrocarbon in steps (B) and (C) is about 20–200% higher than said molar ratio employed in step (A) or, alternatively, step (D).

24. A process in accordance with claim 23, wherein the chloride level in step (B) is about 40–90% lower than said chloride level employed in step (A) or, alternatively, step (D), and wherein the chloride level in step (C) is about 20–300% higher than said chloride level employed in step (A) or, alternatively, step (D).

25. A process in accordance with claim 24, wherein the time period of step (B) is about 0.5 hour to about 15 days and the time period of step (C) is about 0.5 hour to about 15 days.

26. A process in accordance with claim 16, comprising the additional step (X) of preactivating said isomerization catalyst, before it is employed in step (A), by treating of said catalyst with said fluid feed mixture, wherein (α) the molar ratio of hydrogen gas to said at least one saturated feed hydrocarbon in step (X) is at least about 20 percent higher than said molar ratio employed in step (A), or wherein (β) the reaction temperature in step (X) is at least about 5° F. lower than said reaction temperature employed in step (A), or wherein both operating parameters (α) and (β) are applied in step (X).

27. A process in accordance with claim 26, wherein the pressure in steps (X), (A), (B), (C) and (D) is in the range of about 50 psig to about 2,000 psig.

28. A process in accordance with claim 27, wherein said at least one saturated feed hydrocarbon is selected from the group consisting of n-butane, n-pentane, n-hexane, n-heptane, 2-methylpentane, 2-methylhexane, 3-methylhexane, methylcyclopentane, cyclohexane, methylcyclohexane and mixtures thereof.

29. A process in accordance with claim 28, wherein said at least one chlorinated hydrocarbon is selected from the group consisting of chloroalkanes, chloroalkenes and chlorocycloalkanes and contains up to 6 carbon atoms and up to 8 chlorine atoms per molecule.

30. A process in accordance with claim 27, wherein (α) said molar ratio of hydrogen gas to said at least one saturated feed hydrocarbon in step (X) is about 50–500 % higher than said molar ratio employed in step (A), or wherein (β) said reaction temperature employed in step (X) is about 20°–40° F. lower than said reaction temperature in step (A), or wherein both operating parameters (α) and (β) are applied in step (X), and wherein step (X) is carried out for at least for 4 hours.

* * * * *